(12) United States Patent
Jacobs et al.

(10) Patent No.: US 7,452,508 B2
(45) Date of Patent: Nov. 18, 2008

(54) ASPIRATING AND MIXING OF LIQUIDS WITHIN A PROBE TIP

(76) Inventors: Merrit N. Jacobs, 3 Foxboro Ter., Fairport, NY (US) 14450; Zhong Ding, 2 Breezewood Ct., Fairport, NY (US) 14450; Ronald F. Brookes, 55 Union Station Rd., N. Chili, NY (US) 14514-9742

( * ) Notice: Subject to any disclaimer, the term of this patent is extended or adjusted under 35 U.S.C. 154(b) by 234 days.

(21) Appl. No.: 09/993,054

(22) Filed: Nov. 6, 2001

(65) Prior Publication Data
US 2002/0076826 A1 Jun. 20, 2002

Related U.S. Application Data

(62) Division of application No. 09/510,928, filed on Feb. 22, 2000, now Pat. No. 6,641,993.

(51) Int. Cl.
*B01L 3/02* (2006.01)
(52) U.S. Cl. .................. 422/100; 73/863.32; 73/864; 73/864.01; 73/864.11; 366/89; 366/91; 366/21; 222/251
(58) Field of Classification Search .................. 422/100, 422/102, 931, 936, 103; 73/863.32, 864, 73/864.01, 864.11; 366/21, 89, 91, 158.2; 222/231, 232, 251
See application file for complete search history.

(56) References Cited

U.S. PATENT DOCUMENTS

| | | | | |
|---|---|---|---|---|
| 1,547,562 A | * | 7/1925 | Byrd .......................... 422/100 |
| 2,697,945 A | * | 12/1954 | Dovas ...................... 73/864.16 |
| 3,660,037 A | * | 5/1972 | Sokol ........................... 422/73 |
| 3,874,851 A | * | 4/1975 | Wilkins et al. ................ 435/30 |
| 4,119,125 A | * | 10/1978 | Elkins .......................... 141/11 |
| 4,444,062 A | * | 4/1984 | Bennett et al. ............ 73/863.32 |
| 4,679,446 A | * | 7/1987 | Sheehan et al. .......... 73/864.13 |
| 4,780,418 A | | 10/1988 | Kratzer |
| 4,852,620 A | * | 8/1989 | Jakubowicz et al. .......... 141/25 |
| 5,174,162 A | | 12/1992 | Miyake et al. |
| 5,192,511 A | * | 3/1993 | Roach ......................... 422/100 |
| 5,223,226 A | * | 6/1993 | Wittmer et al. ............. 422/100 |
| 5,232,669 A | * | 8/1993 | Pardinas ..................... 422/100 |

(Continued)

FOREIGN PATENT DOCUMENTS

EP 0 005 979 A 12/1979

(Continued)

OTHER PUBLICATIONS

Search Report for corresponding application No. EP 00 30 1088; Date of completion of the search Feb. 28, 2001.

*Primary Examiner*—Brian R. Gordon
(74) *Attorney, Agent, or Firm*—Todd J. Burns

(57) ABSTRACT

Apparatus and a method for mixing a liquid within a disposable aspirating probe tip so that most of the liquid is forced to move past a transition zone between two different inside diameters to cause rotational mixing. The apparatus and method can be used to provide agglutination of blood, which in turn can be used for blood typing. The probe tip can include a single integral piece, or two separate portions. The transition zone can include a sharp demarcation between inside diameters, or a smooth one.

5 Claims, 7 Drawing Sheets

U.S. PATENT DOCUMENTS

| | | | |
|---|---|---|---|
| 5,273,717 A * | 12/1993 | Marvin | 422/100 |
| 5,425,920 A * | 6/1995 | Conti et al. | 422/102 |
| 5,441,895 A | 8/1995 | Jakubowicz et al. | |
| 5,580,529 A * | 12/1996 | DeVaughn et al. | 422/101 |
| 5,665,601 A * | 9/1997 | Kilmer | 436/54 |
| 5,773,305 A * | 6/1998 | Zabetakis et al. | 436/179 |
| 5,811,306 A * | 9/1998 | Komatsu | 436/54 |
| 5,814,275 A * | 9/1998 | Lewis et al. | 422/63 |
| 5,821,436 A | 10/1998 | Bienhaus et al. | |
| 5,851,491 A * | 12/1998 | Moulton | 422/101 |
| 5,891,397 A * | 4/1999 | Greenfield | 422/68.1 |
| 5,919,356 A * | 7/1999 | Hood | 210/85 |
| 2003/0190264 A1 * | 10/2003 | Yiu | 422/100 |
| 2004/0052689 A1 * | 3/2004 | Yao | 422/100 |
| 2004/0071602 A1 * | 4/2004 | Yiu | 422/100 |

FOREIGN PATENT DOCUMENTS

EP          0 849 584 A          6/1998

\* cited by examiner

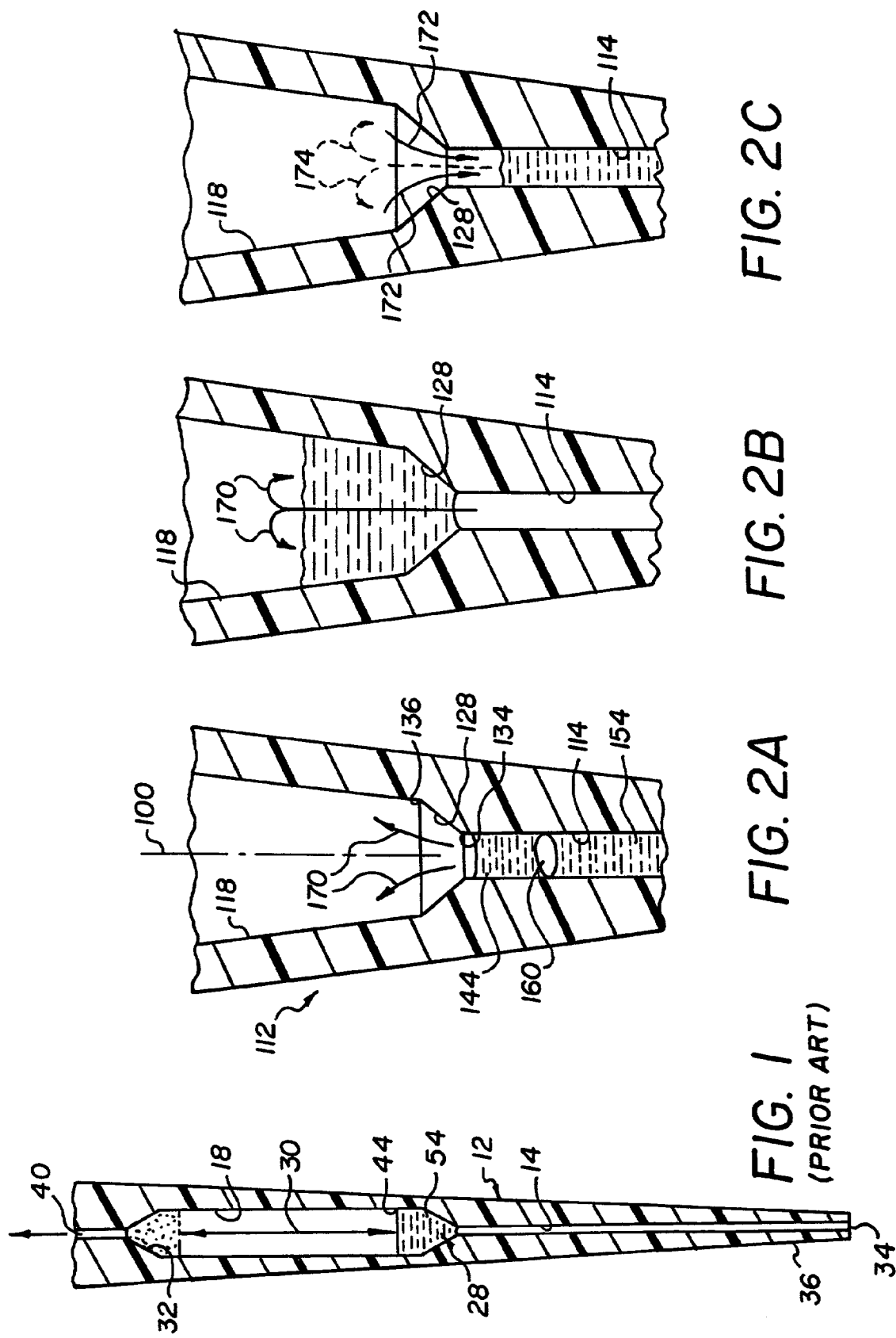

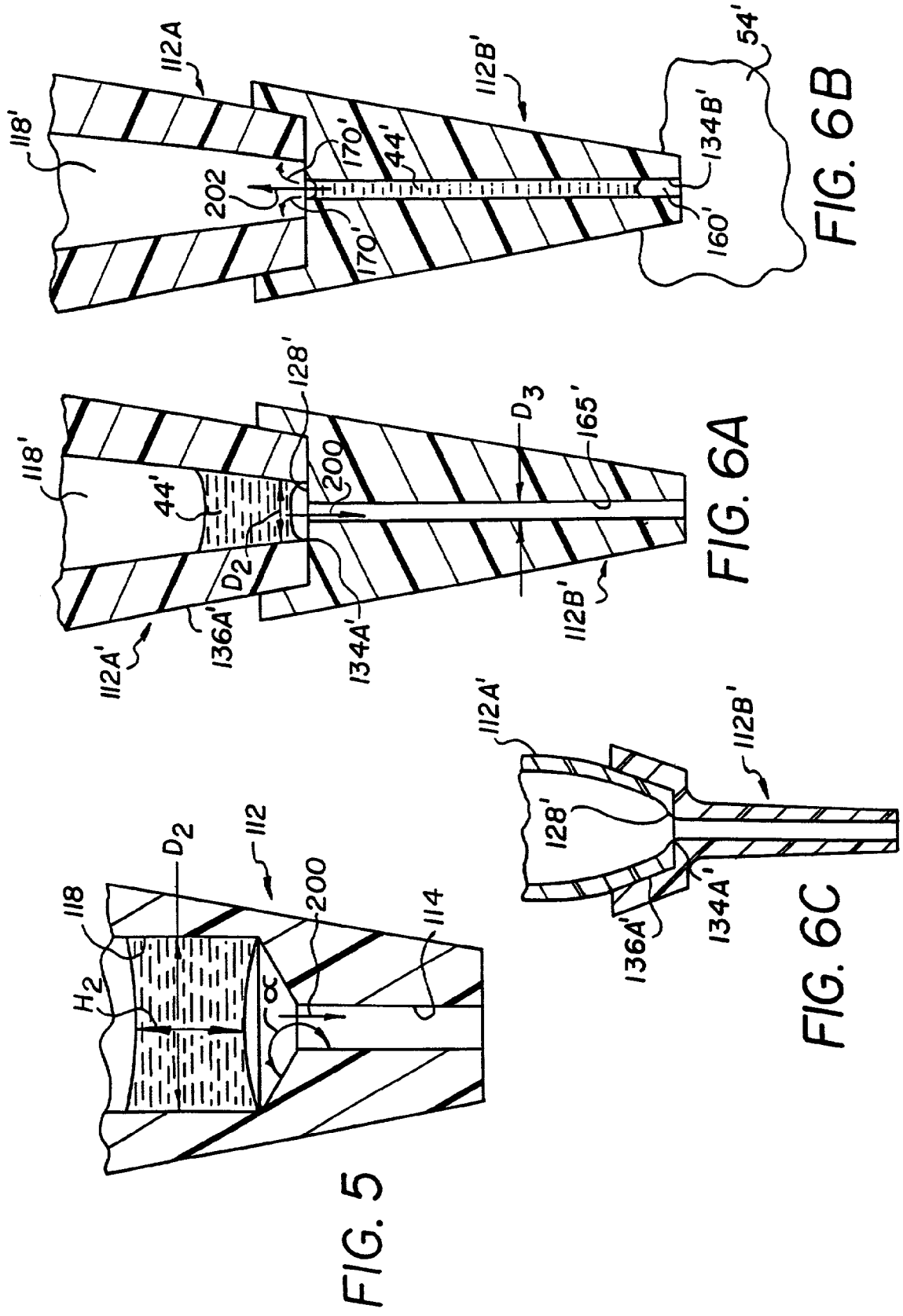

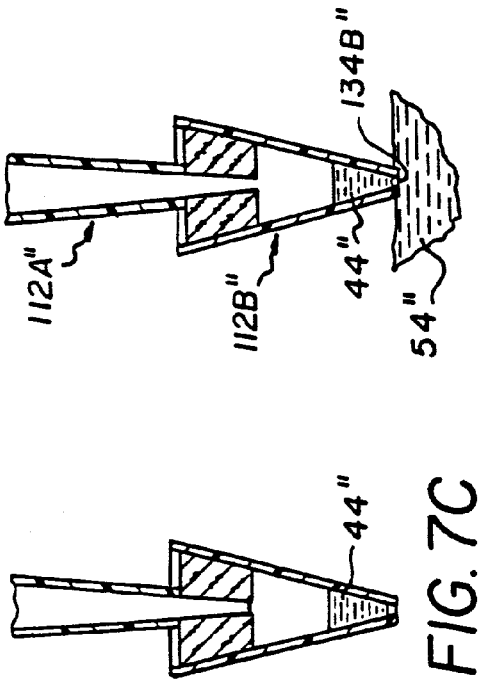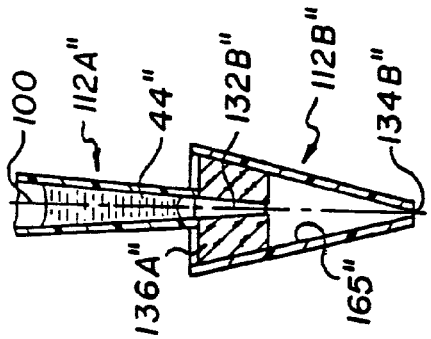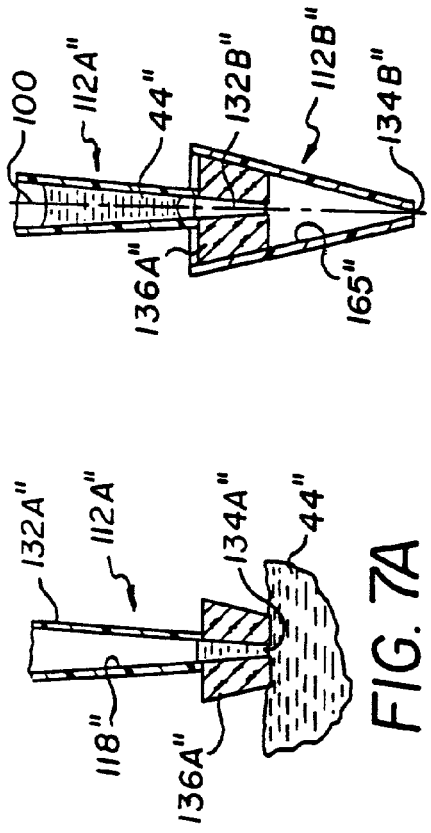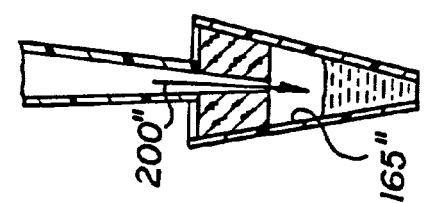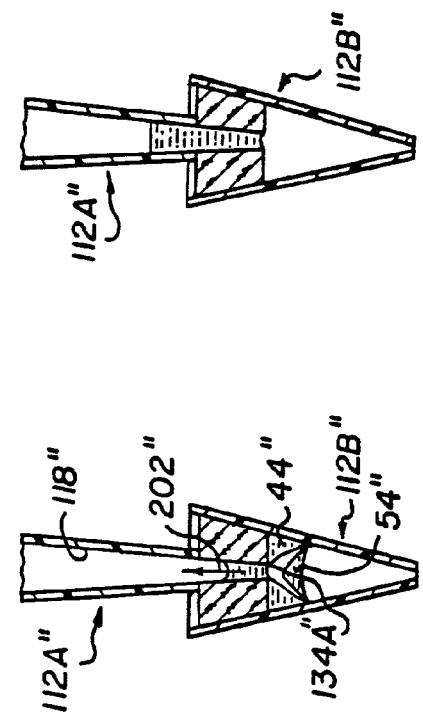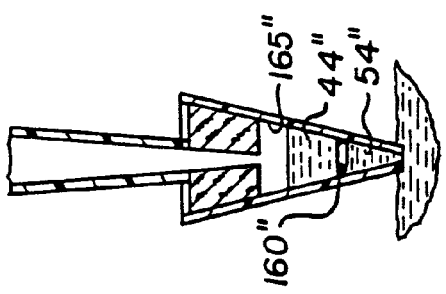

ASPIRATING AND MIXING OF LIQUIDS WITHIN A PROBE TIP

CROSS REFERENCE TO RELATED APPLICATIONS

This application is a divisional of U.S. Ser. No. 09/510,928, filed Feb. 22, 2000, the contents which are hereby incorporated by reference now U.S. Pat. No. 6,641,993.

FIELD OF THE INVENTION

The invention relates to apparatus and a method for mixing two liquids within a tip on an aspirating probe, to ensure a reaction between the liquids.

BACKGROUND OF THE INVENTION

It is known from U.S. Pat. Nos. 5,773,305 and 5,114,162 to mix a fluid sample such as blood and a diluent, inside a probe tip by first aspirating both liquids into the tip, and then drawing said liquids further up into the tip into a mixing chamber having an enlarged inside diameter compared to the rest of the tip. The mixing can be achieved, for example, by reciprocating the mass of liquids up and down numerous times.

In the examples shown in U.S. Pat. No. 5,773,305, the liquids are retained in the enlarged chamber and simply sloshed back and forth in that chamber to achieve mixing. FIG. 3 thereof makes it clear that simply aspirating the liquids into the enlarged chamber past a step discontinuity created by the enlarged inside diameter, is ineffective in creating a mixture. That is, a single movement past the step discontinuity is shown as not mixing the fluids homogeneously. An air bubble can also be included between the liquids when first aspirated. Cross-over contamination between bodies of liquid being aspirated is preferably prevented by ejecting an inert oil shield around the outside of the tip, FIGS. 7 through 11 thereof.

Such a construction is generally equivalent to transferring two liquids from a pipette into a larger diameter container (the mixing chamber) and attempting mixing by sloshing the liquids vertically within the container. Although mixing can occur in such a fashion for relatively large volumes, it is not as effective for small volumes, e.g., volumes that total 100 to 600 microliters. That is, in a constant diameter channel, inertial mixing is reduced if the volumes are small, as here. It is this phenomenon that requires the movement of the liquids back and forth in the mixing chamber, as much as 20 times, to achieve homogeneous mixing. Such reiterations of the mix step are time-consuming, and beg for an improvement.

Furthermore, it is not the case that cross-contamination is preventable only by using such an oil shield. That is, in some cases, the first-aspirated liquid can be removed from the tip simply be repeated washing with a diluent, or by wiping. In any event, should washing prove to be unsatisfactory, there has been a need for a more reliable method of preventing contamination than by using the oil shield. (The oil shield is not guaranteed to form completely around the tip just because a plurality of dispensing nozzles are disposed about the circumference of the exterior of the tip.) Furthermore, some proteins can destroy the shield effect of the oil.

In the examples of U.S. Pat. No. 5,174,162, all the liquids to be mixed are moved completely into the enlarged mixing chamber, completely out of the chamber, then back into it, and so forth. The sharp transition at surface 15 causes turbulent mixing, 16, FIG. 2 thereof. This is a more efficient mixing method than that of the '305 patent. Nevertheless, there are improvements that are needed in such a mixing system as described in the '162 patent. For example, no optimization is described for the geometry of FIG. 2. Nothing is described regarding any use of air bubbles to separate the liquids as they are aspirated. As noted however in the '305 patent, such an air bubble provides an effective prevention against cross-contamination. Yet, any air bubble must be rapidly eliminated during mixing.

Furthermore, the '162 patent is notably deficient in any teaching to prevent cross-contamination when aspirating liquid 6 immediately after liquid 4, between the two liquids within the bulk container of liquid 6. Although the oil shield of the '305 patent might seem to be applicable to the probe of the '162 patent as well, such a shield has disadvantages as noted above. Alternative protection methods against cross-contamination, besides the oil-shield method, are thus desirable.

Yet another disadvantage of the teachings of the '162 patent is that when the two disparate liquids are moved back and forth across the boundary 15, unmixed "tails" of one or both liquids can be left behind as coatings on either the enlarged chamber or the narrower intake portion. Such residual tails do not get mixed when the main body of liquids is moved across boundary 15, so that the tails are undesirable.

Thus, although substantial development has already occurred in probes designed to mix two liquids entirely with the probe, there remains the need for improvements.

SUMMARY OF THE INVENTION

We have devised a mixing method and a probe tip for doing the mixing therein, that provide the above-noted needed improvements.

More specifically, in accord with one aspect of the invention, there is provided a method of mixing a plurality of liquids, comprising the steps of:

a) providing a probe tip with an internal cavity having a plurality of different inside diameters;

b) providing by aspiration a plurality of liquids inside a portion of the probe tip;

c) moving at least most of said liquids back and forth at least several times between a part of said cavity with a smaller inside diameter and a part with a larger inside diameter, said larger and smaller diameters being sufficient to provide a sufficient rotation of liquid as it moves between diameters to cause mixing of said liquids;

the improvement wherein the capillary number resulting from the mixing in step c) does not exceed about 0.01, the capillary number being defined as the ratio of liquid velocity times viscosity and surface tension, so that any tails formed during the mixing step c) are minimized.

In accord with another aspect of the invention, there is provided a method of mixing a plurality of liquids comprising the steps of a) through c) listed above, wherein the improvement comprises that the cavity parts comprise two separate but matable tip portions, and the method further includes the step of mounting a tip portion of one of the inside diameters onto the tip portion of the other inside diameter in-between aspiration of liquids, such that carry-over contamination between liquids is prevented.

In accord with still another aspect of the invention, there is provided a method of mil a plurality of liquids comprising the steps of a) through c) listed above, wherein the improvement comprises the inside diameters each provide a cross-sectional flow-through area of the cavity part, and the cross-sectional flow-through area of the larger inside diameter is at least three times the cross-sectional flow through area of the smaller inside diameter, for maximum mixing efficiency.

In accord with yet another aspect of the invention, there is provided a method of mixing a plurality of liquids comprising the steps of a) through c) listed above, wherein the improvement comprises the larger inside diameter being obtained by i) selecting as a first tip portion a tapered tip at least a portion of which has an inside diameter that is much larger than the smaller inside diameter of the probe tip, and ii) joining the tapered tip to the probe tip having the smaller inside diameter.

In accord with yet another aspect of the invention, there is provided a method of mixing a plurality of liquids comprising the steps of a) through c) listed above, wherein the improvement comprises providing a total amount of liquid in step b) such that if all liquid is moved into the part with the larger inside diameter, the larger inside diameter is greater than the height of the total liquid, but less than twice the height of the total liquid, so that mixing as per step c) is maximized.

In accord with yet another aspect of the invention, there is provided a method of mixing a plurality of liquids comprising the steps of a) through c) listed above, wherein the improvement comprises moving in the step c) at least most of the liquids back and forth at least between the cavity part with the smaller inside diameter and a part of the cavity of a larger inside diameter located at opposite ends of the cavity part of the smaller inside diameter, so that mixing efficiency is enhanced by rotation of the liquid as it moves past the opposite ends, rather than a single end of the smaller inside diameter cavity part.

In accord with yet another aspect of the invention, there is provided a method of mixing a plurality of liquids comprising the steps of a) through c) listed above, wherein the improvement comprises moving in the step c) at least most of the liquids back and forth at least between the cavity part with the smaller inside diameter and a part of the cavity of a larger inside diameter located at opposite ends of the cavity part of the smaller inside diameter, so that mixing efficiency is enhanced by rotation of the liquid as it moves past the opposite ends, rather than a single end of the smaller inside diameter cavity part.

In accord with yet another aspect of the invention, there is provided a probe tip for mixing liquids within the tip after aspiration of the liquids therein to, the tip comprising a wall defining 3 connected cavities of unequal inside diameters one of the compartments being sandwiched as a middle compartment between the other two which form end compartments, each two adjacent cavities being connected by a transition zone wall and the inside diameters being sufficiently unequal in the adjacent 2 cavities as to cause rotational mixing of liquids as they move past the transition zone wall, wherein the transition zone of the one cavity is formed by a variance of the inside diameter that increases in value as the middlemost cavity is transited outward into either of the other two end cavities.

In accordance with yet another aspect of the invention, there is provided a method of determining the strength of an agglutination reaction within a hollow container comprising walls capable of transmitting light at certain predetermined wavelengths, comprising the steps of:

a) providing a mixture of a sample and an agglutinating reagent within a first cavity of the container, the cavity having a first inside diameter, b) transferring the mixture to a second cavity having a second inside diameter substantial smaller than the first inside diameter, c) scanning the liquid within the second cavity during the step b) with a beam of light at the predetermined wavelengths, the 10% portion being that portion closest to the fist cavity;

d) after the scanning step c), detecting the amount of light absorbed within or scattered by the 10% portion by the beam, e) transferring the mixture back into the first cavity, f) repeating steps b)-d) at least once until some agglutinated material has separated from non-agglutinated material, and g) calculating the amount of agglutination from the absorbance or scattering detected in step d).

In accordance with yet another aspect of the invention, there is provided a method of agglutinating blood cells in whole blood, comprising the steps of a) aspirating whole blood into a disposable tip mounted on a probe, said tip having at least two portions with significantly different inside diameters, connected to each other by a transition zone, b) aspirating into the same tip thereafter, an agglutinating reagent, and c) moving said blood and reagent back and forth as a total liquid, first entirely into one of said portions and then entirely into the other of said portions, a sufficient number of times so as to cause coagulation of the cells of the whole blood, and then subsequent separation of plasma from the coagulated cells.

As used herein, "probe tip" or "probe tip portion" means any vessel, disposable or not, into which liquid can be aspirated, mountable on an aspirating probe, that comprises the features noted, namely an orifice, an interior chamber spaced from the orifice, and a passageway connecting the orifice and the chamber. Thus, the tip or tip portion can be a conventional disposable tip such as is shown in U.S. Pat. No. 4,347,875 by Columbus, or even a cup or well with an orifice in the bottom, such as the cup shown in U.S. Pat. No. 5,441,895 but with an orifice in the bottom. The tip can be one integral piece or provided in several portions.

Accordingly, it is an advantageous feature of the invention that more rapid mixing of two liquids aspirated into the tip, takes place within the tip than occurs with conventional devices.

It is a related advantageous feature of the invention that no additional device is needed beyond the tip that is used anyway for aspiration, to provide mixing.

It is another advantageous feature of the invention that, in some embodiments, carry-over contamination between liquids aspirated is preventable by an inexpensive mechanical device that is less time consuming than repeated washing.

A related advantage of the aforesaid mechanical device for preventing carry-over contamination, is that it renders the tip of the invention more manufacturable.

Other advantageous features will become apparent upon reference to the Detailed Description of the Embodiments, when read in light of the attached drawings.

BRIEF DESCRIPTION OF THE DRAWINGS

FIG. 1 is a fragmentary elevational view in section of a probe tip constructed in accordance with the prior art;

FIGS. 2A-2C are fragmentary elevational views in section, similar to that of FIG. 1, but illustrating a method of the invention;

FIGS. 3-5 are fragmentary elevational views similar to that of FIG. 2, but illustrating certain preferred embodiments;

FIG. 6A is a fragmentary elevational view similar to FIGS. 2-5, except it illustrates an alternative embodiment wherein the second tip portion that is added between aspirations, has a narrower inside diameter than the first tip portion;

FIG. 6B is a view similar to that of FIG. 6A, showing the subsequent steps of mixing;

FIG. 6C is an elevational view similar to that of FIG. 6A, but of an alternate embodiment;

FIGS. 7A-7H are elevational views in section similar to FIGS. 6A-6C, except showing a further additional embodiment wherein liquid flowing from the second tip portion to the first tip portion is constrained to move into a narrower, rather than wider, diameter for mixing;

DESCRIPTION OF THE PREFERRED EMBODIMENTS

Figure 3:
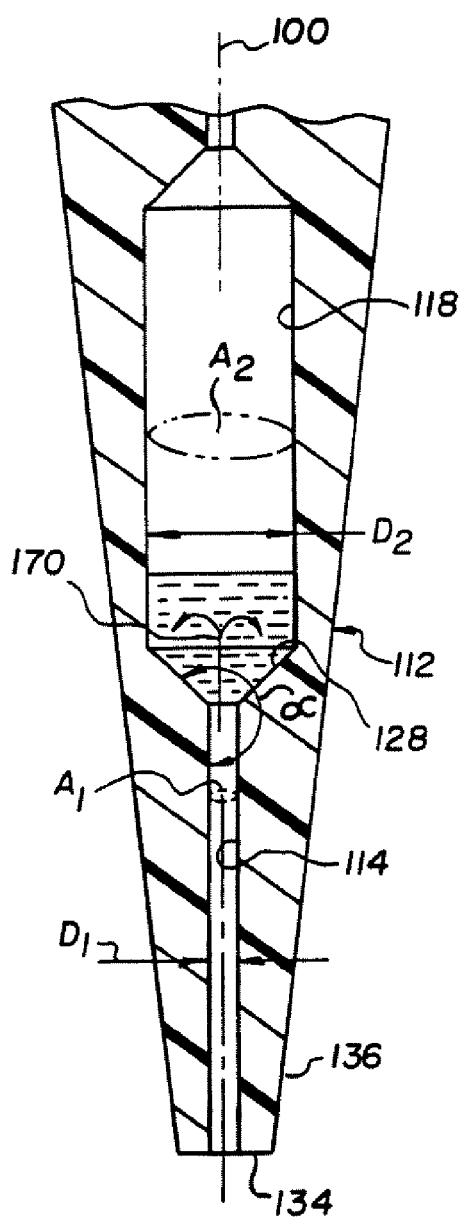

The invention is hereinafter described in connection with certain preferred embodiments, wherein mixing of one or two liquids, one of which is body liquid, is achieved using a disposable tip with one or two portions of preferred shapes, the second being preferably separate from and added to the first to prevent carry-over contamination of a the second liquid after the first liquid is aspirated, wherein the first liquid is preferably blood and the second is an agglutinating solution, and mixing is accomplished at preferred flow and shear rates, preferably to allow blood typing to occur. In addition, the invention is useful regardless of how many and what shape portions the tip is divided into, whether a second portion is separately added or already present, or is used to prevent contamination or not, what the liquid compositions are, what order they are added, what the flow and shear rates within the tip are, and what the end result of the mixing is; provided that the tip shape induces mining by forcing the mixing liquids to move between cavity parts with differing diameters sufficient to cause rotational mixing of the liquids as they flow between the cavity parts. That is, it is repeated movement between the transition in diameters that causes rapid mixing, rather than sloshing the liquids within a constant inside diameter. Thus, the reagent interacting with the body liquid can be reagents for an immunoassay, for example.

The less successful approach is that of the prior art, shown here as FIG. 1. This is substantially the teaching of the aforesaid U.S. Pat. No. 5,773,305. In such an arrangement, an aspiration probe 12 comprises a narrow cavity or passageway 14 that leads from an aperture 34 at end 36, to a mixing cavity 18 having a significantly wider inside diameter than that of cavity 14. A transition region 28 with relatively sharp demarcations is provided between the two diameters. A partial vacuum is applied at passageway 40 to aspirate first a liquid 44, and then a second liquid 54, into cavity 18, with or without a bubble (not shown) between them. As shown in the original '305 patent, the first time both liquids are moved from passageway 14 into cavity 18 fails to produce complete mixing, since the two liquids still remain separated. The actual mixing is achieved by oscillating the two liquids, arrows 30, within cavity 18, from an end at transition zone 28, to the opposite end 32 of cavity 18. Additionally, an oil shield is taught as useful on the exterior surface 36 of the probe, to prevent liquid 44 from coating surface 36 and contaminating bulk liquid 54 when the latter is aspirated. As noted above, such a techniques requires as much as 20 oscillations, arrows 30, to achieve mixing.

In both the '305 patent and the instant invention, movement of liquids within the tip is achieved while the tip is on a pipette (i.e., aspirating probe), by actuation of a piston within a piston cylinder, not shown, to create a partial pressure or partial vacuum. For example, the piston can be operated manually. In the present invention, the aspirating probe is shown as 600 in FIG. 4.

In accordance with the invention, FIGS. 2A-2C, the number of oscillations can be reduced to as few as three, by simply forcing most of the liquid to flow past the transition zone 128 each time. This, in turn, is ensured by forcing most of both liquids to flow from one cavity adjacent the transition zone, into the other cavity so adjacent, and then back. As used herein, "most of the liquids" being moved means, at least 90% of the liquids.

Figure 4:
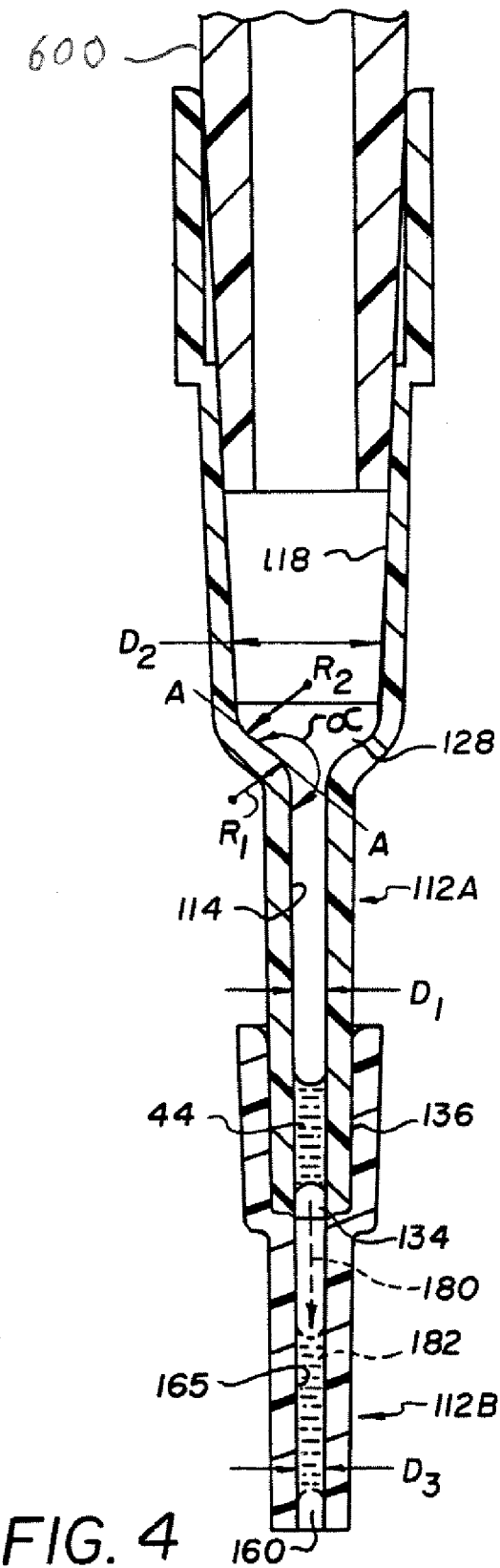

More specifically, a probe preferably in the form of a disposable tip 112, is constructed substantially the same as that of the prior art, with a narrower cavity 114 leading to a wider cavity 118 connected to the narrower one by a transition zone 128. A common axis of symmetry 100 preferably extends through both cavities. In this example, the transition zone is defined by relatively sharp edges 134 and 136 at the junction with the respective cavities. "Relatively sharp" leans, having a radius of curvature at the junction that is less than 25 microns. Any radii greater than that tend to produce a smooth transition between zone 128 and the respective cavities. In fact, a smooth transition through the use of such greater radii of curvature is preferred, but not essential, as such a smooth transition gives better results when blood agglutination for blood typing is the goal of the mixing. That is, the smooth transition using greater radii of curvature is less likely to cause the agglutinates to be broken up, all other things such as bulk flow rates, being equal. An example of a smooth transition using such greater radii of curvature is shown in FIG. 4. For example, $R_1$ and $R_2$ for FIG. 4 can be, respectively, 1.2 mm each.

Since the structure is generally the same as for FIG. 1 of the prior art, the main distinction, at least with respect to FIGS. 2A-2C, is in the use of probe 112. That is, a first liquid 144 is aspirated into cavity 114, followed by an air bubble 160. Thereafter, second liquid 154 is aspirated in so that both are still in cavity 114, FIG. 2A.

Next, most and preferably all of both liquids are aspirated past zone 128 and into cavity 118, FIG. 2B. Transition zone 128 produces sufficient rotation, arrows 170, of the liquids as to start them to mix. As shown in FIG. 1, however, just this step is not enough. Next, most and preferably all of the liquids are ejected from cavity 118 past transition zone 128 and into cavity 114, arrows 172, FIG. 2C. Still further, the process is repeated, phantom arrows 174, until complete mixing has occurred. Depending on the liquids involved, only three passages from cavity 114 into cavity 118 may be necessary for complete mixing, although more can be used.

FIG. 3 illustrates certain preferred parameters for optimal mixing in general. Probe 112 has an aperture 134 and an exterior surface 136 adjacent to that aperture, similar to that of the prior art. However, the cross-sectional flow-through area $A_2$ of cavity 118, provided by inside diameter $D_2$, is preferably no smaller than nine times that of the cross-sectional flow-through area $A_1$ provided by inside diameter $D_1$, of cavity 114. Furthermore, the diameters $D_1$ and $D_2$ are generally constant so that their respective cavities are cylindrical. Thus, $D_2$ is preferably at least equal to three times $D_1$.

Useful examples of $D_1$ and $D_2$ include, e.g., 0.8 mm and 3.2 mm, respectively, for use with a total height $H_2$, FIG. 5, of about 3 mm.

Still further, to aid in the dispersal of air bubble 160, FIG. 2A, during mixing, the wall surface of at least cavity 118, and optionally also cavity 114, is selected from materials that are easily wetted by the liquids in question, that is, produce a low contact angle at the meniscus. Thus, the materials used for the surfaces are a function of the liquids to be mixed, as is well-known. Most preferably, for maximum dispersal of the air bubble (present to aid in preventing cross-contamination between liquids during the second aspiration), the capillary number for the system does not exceed 0.001, where capillary member, as is conventional, equals liquid velocity of movement, arrow 170, divided by surface tension of the liquid mixture.

However, it is not essential that an air bubble be present to avoid contamination. An oil shield can be used as in the '305 patent, or alternatively, probe 112 can be wiped off before aspirating the second liquid. In that case, the capillary number can be larger, but preferably not exceeding 0.01, since above that, the movement of the liquids between cavities can product "tails" of liquid remaining in the exit cavity that delay or even ruin the mixing process.

If an air bubble is used, a further consideration is that the size or volume of the bubble must be less than that which will prevent mixing of the liquids as they flow past the transition zone. Thus, the air bubble must not be so large that, after aspiration of the probe contents into cavity 118, FIG. 3, the bubble (not shown in FIG. 3) continues to totally separate the two liquids—that is, has a diameter equal to the inside diameter of cavity 118. Thus, for FIG. 3, the bubble volume must be less than $\pi(D_2)^3/6$.

In the event the mixing is being done for blood typing, a further factor is important in addition to those noted above. That is, to prevent the rotational action, arrows 170, FIG. 3, from significantly breaking apart the desired blood cell agglutination, the flow velocity in either direction past the transition zone 128 is preferably that which provides a shear rate along the wall which does not exceed about 20 sec$^{-1}$. This, of course, is also a function of the viscosity of the liquids, of the diameters $D_1$, $D_2$, and of angle alpha.

Regardless of the end use of mixing, the embodiment of FIG. 3 can also be used by coating either cavity 114 or 118 in dry form, with the reagent that is to react with the body liquid, so that only one liquid namely the body liquid, need be aspirated in at aperture 134. Thus, the agglutinating reagent solution can be provided during manufacturing by coating either or both cavities 114 or 118. This coating is then redissolved when the whole blood is aspirated into the appropriate cavity.

For other uses, other reagents, such as an antibody for an immunoassay, may be permanently attached to the cavity walls.

It is not essential that the probe be all in one piece, or that contamination be prevented by only an oil shield or by wiping. Instead, FIG. 4, it is useful to have the probe comprise two portions, 112A and 112B one of which (112B) has an inside diameter that is different from, e.g., smaller than, at least part of the inside diameter of the other portion (112A), and which fits over the other portion adjacent aperture 134. The purpose is to allow the portion that over-fits the first portion, to cover up the exterior surface 136 adjacent to aperture 134 where residual first liquid 44 might remain. As shown, inside diameter $D_3$ of cavity 165 of portion 112B is substantially identical to diameter $D_1$, but less than dime $D_2$, of portion 112A. In use, liquid 44 is aspirated into portion 112A with portion 112B absent. Portion 112B is then mounted onto portion 112A with a sliding friction fit. At this point, liquid 44 is moved down, arrow 180, into portion 112B to the phantom position 182, leaving an amount of air at 160 to form an air bubble in the next step. That step is to move the probe of combined tip portions so as to insert only portion 112B into a bulk quantity of liquid 54 (not shown). Aspiration then causes liquid 44 at position 182, bubble 160, and an amount of the second liquid to be aspirated in the probe. When the desired amount of the second liquid is present, the probe is removed from the bulk liquid 54, and mixing proceeds as described above using repeated movement of most of the liquids past transition zone 128.

This construction ensures both that residual first liquid amounts on portion 112A are prevented from contacting said bulk liquid 54, and that the resulting length of portions 112A and 112B are easily moldable.

In this embodiment, and any embodiment using a smooth transition between zone 128 and the two cavities provided by the radii of curvature $R_1$ and $R_2$, angle alpha described above is measured against the tangent line A-A drawn to a point on the wall of zone 128 that is between the definition of the wall provided by the two radii.

In FIG. 5, another preferred aspect of the probe 112 is illustrated. That is, cavity 118 of portion 112 or 112A has a diameter $D_2$ that is selected to be larger in value than the height $H_2$ of the total liquids aspirated thereinto, one those liquids have been moved into cavity 118. The advantage of this relationship is that it has been found to enhance the mixing efficiency. At the same time, however, 12 should be less than twice $H_2$, as otherwise the volume in cavity 118 becomes so thin that it is in danger of bursting at the middle when pressure is applied to push the liquid, arrow 200, into cavity 114. Such bursting will of course prevent transfer of the liquid across the mixing transition zone.

Thus, if all of the preferred features are utilized as described above, it has been found that a whole blood sample and an agglutinating solution can be thoroughly admixed after only three cycles of drawing most of the liquids into cavity 118 and returning most of the liquids to cavity 114.

As noted above, when the probe comprises two portions, it is not essential that the inside diameter of the added-on portion equal the inside diameter of the probe portion that is covered. The remaining embodiments illustrate wherein, in fact, this is not the case. Parts similar to those previously described bear the same reference numeral to which the distinguishing mark ' or " is appended.

Thus, in the embodiment of FIG. 6A, the second portion 112B' has an inside diameter $D_3$ for cavity 165' that is considerably smaller than inside diameter $D_2$ of cavity 118'. In effect, probe 112' is now divided into two separable portions 112A' and 112B' having cavities 118' and 165' which between them provide the transition zone 128' that causes mixing. That is, zone 128' is formed by an external angle alpha (shown in FIG. 5) which is 270°.

In use, liquid 44' is aspirated into portion 112A' by itself. Portion 112B' is then affixed to portion 112A' as shown, FIG. 6A, and liquid 44' is pushed down into portion 112B', arrow 200. The probe is then moved so that portion 112B' is inserted into a bulk quantity of liquid 54', preferably with an air bubble 160' at aperture 134', FIG. 6B. Aspiration, arrow 202, causes all of liquid 44', bubble 160', and liquid 54' to move through cavity 165', past transition zone 128', and into cavity 118', thus starting mixing by rotation, arrows 170'. The oscillating movement of all the liquid via arrows 200 and 202 is then repeated as many times as is needed to complete the mixing.

Alternatively, FIG. 6C, the transition zone provided by the add-on portion 112B', when placed around exterior surface 136A' adjacent aperture 134A', can be a smooth transition zone 128' in the manner of the embodiment of FIG. 4. In such a case, care needs to be taken to ensure that a proper match of the inside diameters of portions 112A' and 112B' occurs at aperture 134A', so that indeed the transition in inside diameters is a smooth one. At the same time, however, the smaller inside diameter remains with probe portion 112B', rather than portion 112A', except where they match substantially exactly at aperture 134A'.

The opposite of FIGS. 6A and 6B is illustrated in FIGS. 7A-7H. That is, the inside diameter of the added-on, second tip portion is substantially larger, at the transition zone, than the inside diameter of the first tip portion already used to aspirate liquid. Additionally, this embodiment illustrates that the two cavities adjacent the transition zone need not be cylindrical, but can be tapered instead along their axis of symmetry 100, FIG. 7B.

Thus, FIG. 7A, probe portion 112A" comprises a conical cavity 118" extending from an aperture 134A", to an upper portion 132A" that connects to a pump, not shown, the inside diameter of cavity 118" increasing with increasing distance from the aperture. To allow the two portions 112A" and 112B" to join together, the exterior surface 136A" adjacent to aperture 134A" is enlarged, also with a tapered shape, such as by securing a cork collar to the rest of the portion 112A". The inside diameter at aperture 134A" is relatively small, e.g., about 1 mm.

The second probe portion 112B", FIG. 7B, has an upper portion 132B" shaped to frictionally mate with surface 136A", that is, with an enlarged inside. diameter. Portion 112B" tapers down to a lower portion at aperture 134B" producing a cavity 165" having an inside diameter that is greatly reduced from said enlarged inside diameter, and in fact, preferably is about the same as that of aperture 134A".

The use of this embodiment is similar to that described for FIGS. 6A-6B. Thus, portion 112A" by itself is inserted into a bulk quantity of liquid 44" and an aliquot is aspirated, FIG. 7A. Next, probe portion 112B" is fitted over the surface 136A" of the collar, FIG. 7B. After that, liquid 44" is pushed or ejected from portion 112A" into the cavity of portion 112B", FIG. 7C.

Next, FIG. 7D, the combined probe has aperture 134B" of portion 112B" inserted into a bulk quantity of liquid 54", and that and an air bubble 160", FIG. 7E, is aspirated into cavity 165".

The stage is now set for the actual mixing steps. That is, FIGS. 7F-7H, all of the liquid is aspirated and ejected back and forth past the transition zone created by the narrower inside diameter at aperture 134A". FIG. 7F, it is first drawn into cavity 118", arrow 202", to produce the condition shown in FIG. 7G. It is then ejected back into cavity 165", FIG. 7H, arrow 200", so that rotational mixing occurs. This process is repeated as necessary, until the two liquids become homogeneous, or as homogenous as is possible, given the nature of the liquids.

In all of the embodiments above wherein a second probe portion 112B is fitted onto the first portion 112A prior to aspirating a second liquid, another alternative, following such second aspiration and aspiration of all liquids into the first portion, is to remove the second portion and to fit onto the first portion in the place of the second, a clean third portion of equal, smaller, or larger inside diameter, for the purpose of aspirating into the probe yet another, third liquid in a manner similar to the aspiration of the second liquid.

Additional mixing transitional zones between unequal inside diameters can be provided—that is, it is not essential that there be only two adjacent compartments of varying inside diameters. Indeed, a probe tip that comprises three such compartments serially connected, FIGS. 8-9, has proven to be most efficient in mixing, of all the embodiments described herein. Most preferably, in such an arrangement the middlemost compartment has the smallest inside diameter at the transition zone. Parts similar to those previously describe bear the same reference numeral, to which the distinguishing superscript suffix''' has been appended.

Figure 8:
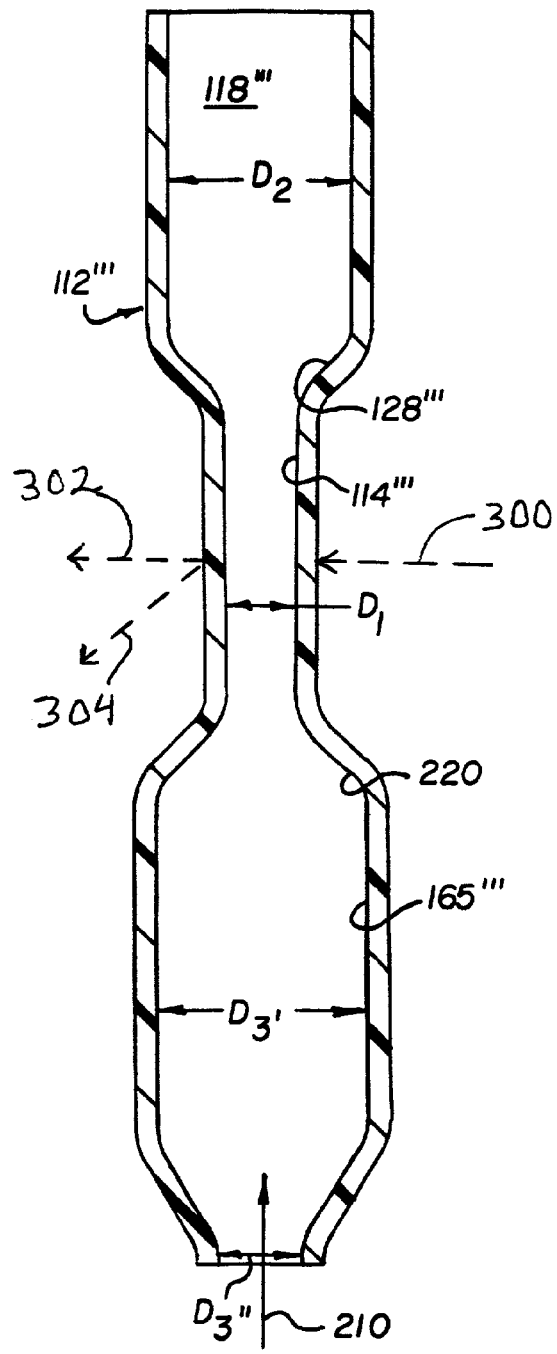
FIGS. 8 and 9 are elevational views in section similar to that of FIG. 4, but showing still further embodiments of the invention.

Thus, FIG. 8, like the design of FIG. 4, probe 112''' comprises an upper portion or cavity 118''' that is mounted onto the permanent probe (FIG. 4), and a lower cavity 114''' integrally connected to cavity 118''' by a transition zone wall 128''', the inside diameter $D_2$ of cavity 118 being larger than $D_1$, and preferably at least equal to three times $D_1$. An additional cavity 165 is provided at exterior portion 136''' of cavity 114, with aspiration occurring at arrow 210, also as described for FIG. 4. However, cavity 165''' is integrally connected to cavity 114''' in that all 3 cavities are formed from a common wall, preferably one that is molded. Further, inside diameter $D_3$ of cavity 165''' is significantly larger than inside diameter $D_1$, creating a transition zone 220 not present in the embodiment of FIG. 4. The value of $D_3$, like that of $D_2$, is selected to cause rotational mixing when most, and preferably all, of the liquids aspirated into tip 112''', is moved from cavity 114''' into cavity 165''' past transition zone 220. Hence, like $D_2$, $D_3'$ is most preferably at least equal to three times $D_1$, $D_3$ can be the same as or different from $D_1$.

Although it is not essential, the inside diameter of cavity 165''' can be narrowed to $D_3"$ at the end into which liquid is first aspirated, arrow 210.

Figure 9:
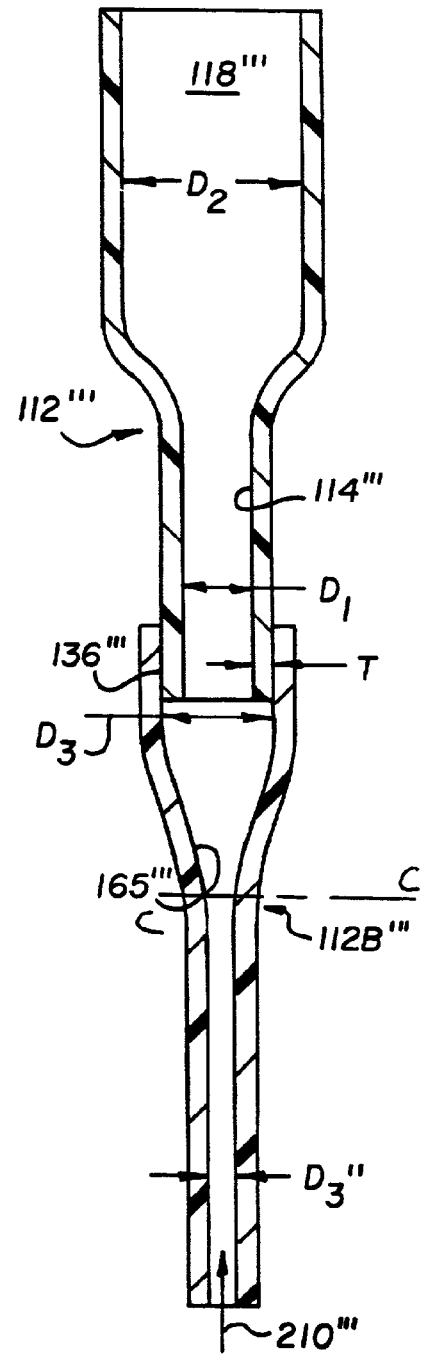

Additionally, as shown in FIG. 9, cavity 165''' of tip 112''' can be formed by the wall of tip portion 112B''', removable as in the embodiment of FIG. 4, so that portion 112B''' can be added after the first liquid is aspirated, and portion 112B''' covers any first liquid remaining on exterior surface 136'''. Aspiration of a second liquid then occurs as shown by arrow 210''', FIG. 9. However, unlike the FIG. 4 embodiment, inside diameter $D_3'$ at the junction of the cavities 114''' and 165''', is greater than the inside diameter $D_1$, rather than equal thereto as in FIG. 4, creating a transition zone 220''' similar to zone 220, FIG. 8, effective to cause liquids to rotationally mix as they move from cavity 114''' into cavity 165'''. In this example, $D_3'$ at the transition zone equals $D_1$+twice the value of T, where "T" is the thickness of the wall providing exterior surface 136'''. In such an example, $D_3'$ may or may not be at least equal to three times $D_1$, depending on the value of T.

As in the case of the embodiment of FIG. 8, the inside diameter of cavity 165''' can be narrowed to $D_3"$ a the end into which liquid is first aspirated.

It is the embodiments of FIGS. 8 and 9 that have proven to be most efficient in mixing, that is, in producing complete mixing in the fewest cycles of repeated back and forth movement past the transition zones. For example, the embodiment of FIG. 9 produced complete mixing of two liquids totaling 20 microliters in only 7.5 cycles of such back and forth movement, at a flow rate of 50 microliters per sec., in about 10 sec.

Agglutination Reactions

As noted above, a preferred use of this mixing action is to produce sufficient blood cell agglutination as to allow blood typing. To that end, one of the liquids is, of course, whole blood and the other is a solution of agglutinating reagent, aspirated into the tip, in either order. Any such solution can be used. A highly preferred example comprises a 3% bovine serum albumin in a 0.1 molar phosphate buffered saline solution containing anti-B IgM clones formulated from tissue culture supernatant (1, 20, and 31 µg/ml concentrations) plus 0.004% FD&C blue dye number 1. All concentrations are % by weights.

It is not necessary that the detection of a strong, weak, or negative reaction of such blood typing be done outside of the mixing tip. Instead, it can be achieved by detecting the amount of agglutination separation within the tip, and thus the strength of the blood typing reaction.

Turning to FIG. 8, this detection is preferably done by scanning for absorbance or light scattering at a position in narrower tip portion 114". (Any other embodiment of the invention can also be used.) That is, at the position of arrow 300, an appropriate optics such as a conventional fiber optics is used to deliver light of a predetermined wavelength that is then transmitted into the tip. The amount of light that is absorbed, measured approximately 10 minutes after mixing has been completed, is then detected as shown schematically by arrow 302, or the amount of light scattered is detected as shown by arrow 304. The results differ depending on how much agglutination has occurred, as shown below. If absorbance is used, suitable wavelengths include 540 nm, and/or 830 nm The former is particularly useful since that is the peak absorption of hemoglobin. Detection of the amount of light scattered, as at 304, is particularly useful to avoid interference from any hemolysis.

Figure 10:
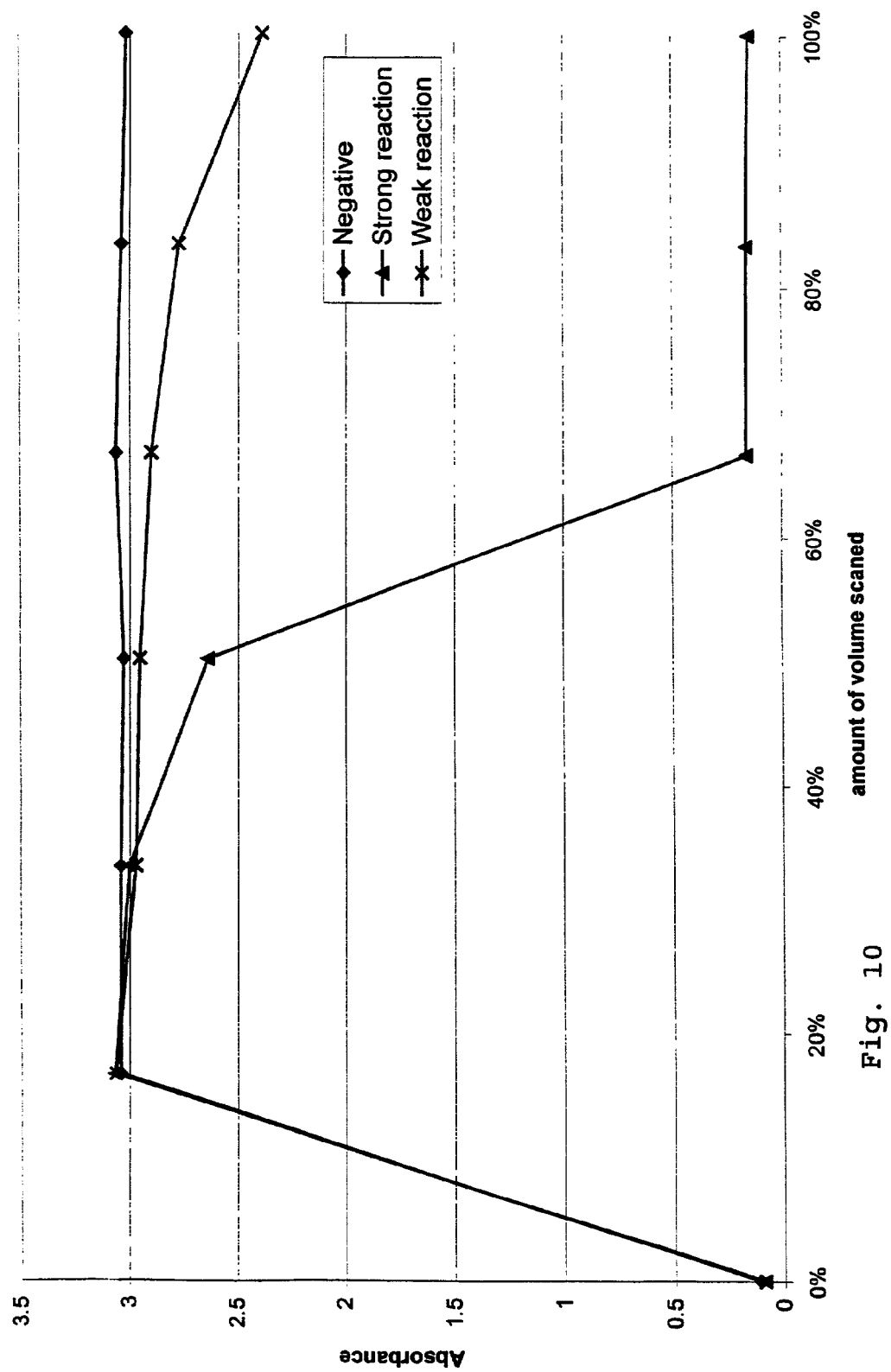
FIGS. 10 and 11 are plots of absorbance versus amount of liquid scanned by a light beam scanning through the tip, to illustrate a method of detecting the strength of an agglutinating reaction.
Figure 11:
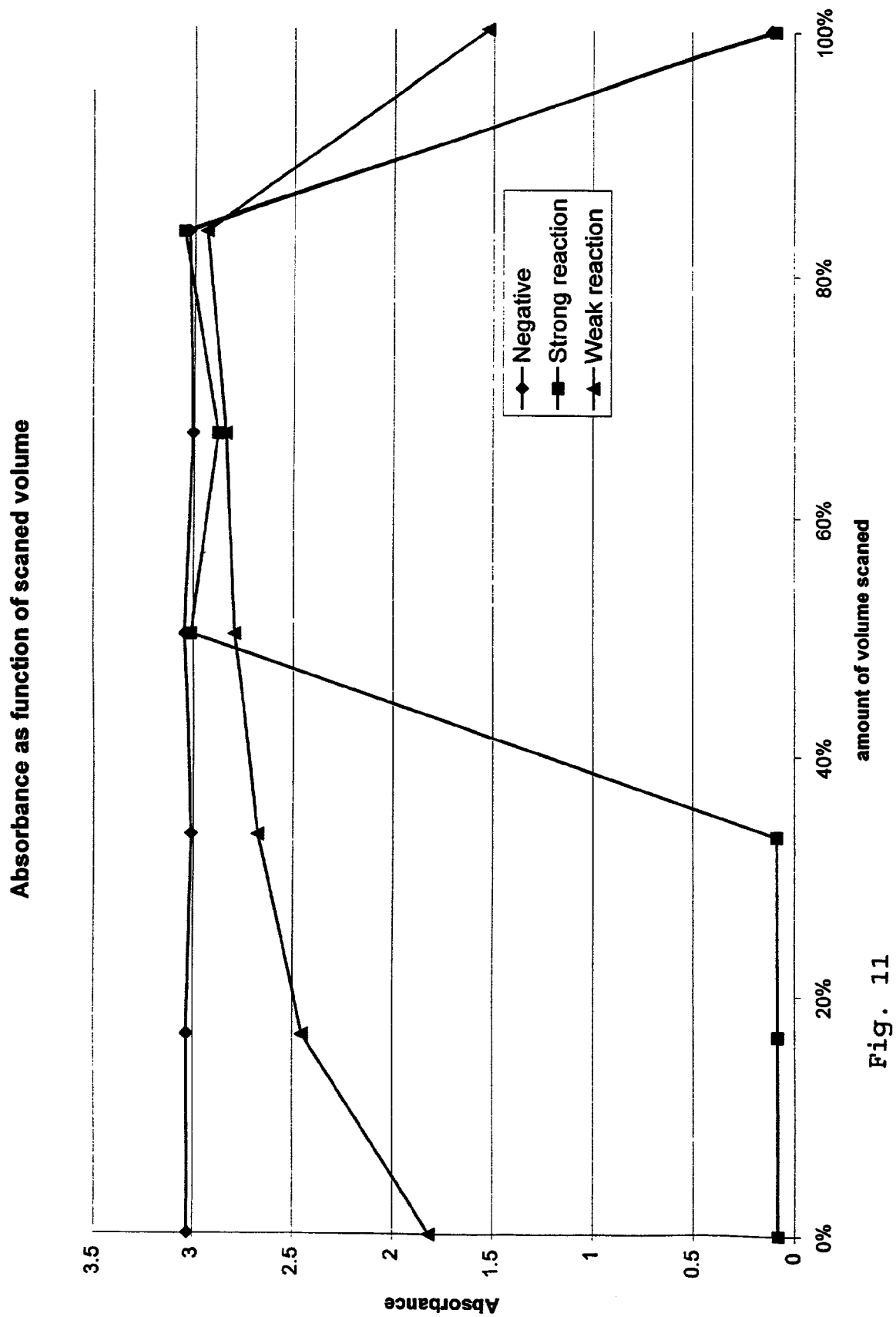

FIGS. 10 and 11 illustrate the method using absorbance and an illuminating wavelength of 540 mm In the case of FIG. 10, the liquid is passed down from portion 118''' to portion 114''', after 10 minutes have passed after it has been mixed sufficiently. At the zero to about 18% of the volume that passes, the amount of absorbance rises from zero due to the passage of air. After that, only liquid is passed by the scanner, and the first part of that liquid is very absorbent, regardless of whether the reaction is negative, weak, or strong. However, after about 50% of the liquid has been scanned, the results deviate depending on the amount of agglutination achieved. A strong reaction clumps the red cells so well that after about 65%, the volume is essentially free of cells and is clear. A weak reaction has less absorption, but still much more than the strong, after 65% of the volume scanned.

Alternatively, the liquid can be moved upward from portion 165'''. into narrower portion 114''' and on upward into portion 118''', to do the scanning. The results are shown in FIG. 11. Differentiation of the results occurs when from zero to 18% of the volume has been scanned. That is, the first portion to flow past the scanner is the liquid portion free of red cells, in the event of a strong reaction, because almost all of the cells have coagulated together. But in the case of the weak reaction, some red cells are still unagglutinated and remain in that first portion of the volume, as shown by the middle curve of FIG. 11.

It is not only blood typing agglutination that is useful as an agglutination reaction in the tip of the invention. Agglutination caused by a coagulating reagent allows separation of the cellular fraction of whole blood from the plasma, to occur in the tip. That is, when the agglutinating reagent is selected from conventional coagulating reagents such as a polyelectrolyte, eg, polylysine, or an antibody such as anti-glycophorin, the mixing within the tip as described above will not only cause coagulation of all the red cells, but it will also lead to a physical separation of those coagulated cells from the plasma. The cells settle to the bottom of the tip, e.g., tip portion or cavity 165''' of FIG. 9. At this juncture, those cells can then be expelled by dispensing them out of the orifice of the tip, leaving only plasma remaining behind. That plasma can then be dispensed onto a suitable platform for testing, for example, into a well or cup adapted for immunoassay, such as is described in U.S. Pat. No. 5,441,895.

The following are non-limiting working examples of the mixing steps of this invention:

EXAMPLE NO. 1

A probe was constructed having two capillaries with different inner diameters. The smaller capillary had an inner diameter of 0.557 mm. The larger capillary had an inner diameter of 2.29 mm. The length of the smaller capillary was 41 mm, which holds up to 10 micro-liter of fluid. The larger capillary had a length of 30 mm.

A type B blood of 4 microliters was aspirated from the bottom end of the small capillary by the pump. The pump then continued to withdraw 1 micro-liters of air in the small capillary. 4 micro-liters of the agglutinating reagent described above was aspirated thereafter and the air bubble separated the two liquids in the smaller capillary.

The pump was then driven to move all the fluids across the transition zone between the small and large capillary with a flow rate of 0.5 micro-liter/second. Once in the larger capillary, a spherical air bubble was created by the surface tension, and the two liquids started to encounter and mix. As the pump drove the fluids to flow down into the smaller capillary with a flow rate of 0.5 micro-litter/second, the bubble was eliminated.

The mixture of the two fluids was oscillated between the two capillaries with a constant flow rate of 0.5 micro-liters/second. The agglutinated structure formation was visible at the end of the first cycle of this motion. Phase separation was very significant at the end of the second cycle in the small capillary, with clear supernatant in the up portion and the agglutinated cell structure in the bottom portion. Some very small agglutinated cells were still visible in the supernatant at this stage. The phase separation was completed by the end of the third cycle, with almost zero cell structure left in the supernatant.

The total time period for the three cycles was 2 minutes. Weaker reactions can be expected to take longer.

Once complete mixing has been achieved, it is then necessary, of course, to achieve a determination of the blood type from the agglutinated results. Although that is not part of this invention, one method of doing this is to make a visual observation of light transmittance through the mixture to determine the amount of agglutination within a fixed time of the agglutination reaction. A chart is used for comparison, and the user estimates the blood type from the amount of clumping or agglutination observed in whichever probe portion that the combined liquids are in at the time.

EXAMPLE 2

A probe was constructed similar to shown in FIG. 9, except that the tip portion 165''' was cut off at line C-C to create a cone-shaped tip portion having an inside diameter at $D_3$ of about 2.54 mm, and at cut line C-C of about 1 mm, with a cone angle of about 20 degrees and a length of 10 mm. Tip portion 114''' had a length of about 15 mm and an inside diameter $D_1$ of about 1 mm. Tip portion 118''' had a diameter $D_2$ of about 4.7 mm. Blood in an amount of 10 microliters was aspirated into the entire tip ensemble through cone portion 165''', after which the cone was wiped clean. Then 10 microliters of reagent were aspirated into the tip in the same manner, producing a total liquid volume of 20 microliters. This total volume was then moved back and forth so as to proceed entirely into portion 118''' and then entirely into portion 165''', and so forth, until mixing was complete. This required 7.5 repetitions (cycles) at a flow rate of 50 microliters per sec. Total displacement of fluids was 40 microliters in each direction of motion, and the time required for complete mixing was about 15 sec.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A combination aspirating probe, probe tip, and pump, comprising:
   a probe tip for mixing liquids within the tip after aspiration of the liquids therein, said tip comprising:
   an end portion adapted to engage an aspirating probe,
   a wall defining three connected cavities of unequal inside diameters, a compartment being formed by a middlemost cavity sandwiched as a middle compartment between the other two cavities which form end compartments, each two adjacent cavities being connected by a relatively sharp transition zone wall having a radius of curvature of less than 25 microns and said inside diameters being sufficiently unequal in said adjacent two cavities as to cause rotational mixing of liquids as they move past said transition zone wall,
   wherein said transition zones of the middlemost cavity is formed by a variance of said inside diameter that increases in value as the middlemost cavity is transited outward into said other two end cavities;
   an aspirating probe, wherein the probe tip is adapted to fit onto the end of the aspirating probe; and
   a pump for creating a partial pressure or vacuum.

2. A combination aspirating probe, probe tip, and pump as claimed in claim 1, wherein the pump is a piston and piston cylinder pump.

3. A combination aspirating probe, probe tip, and pump as defined in claim 1, wherein one of said end cavities is defined by a wall portion removably mounted on a wall defining said middlemost cavity.

4. A combination aspirating probe, probe tip, and pump as defined in claim 1 or 3, wherein the inside diameter of at least one of said end cavities is at least equal to three times the value of the smaller of said differently valued inside diameters.

5. A combination aspirating probe, probe tip, and pump as claimed in claim 1, wherein both transition zones of the middlemost cavity are formed by a variance of said inside diameter that increases in value as the middlemost cavity is transited outward into each of said other two end cavities.

* * * * *